(12) United States Patent
Ito

(10) Patent No.: US 7,672,041 B2
(45) Date of Patent: Mar. 2, 2010

(54) OPTICAL FIBER LIGHTING APPARATUS

(75) Inventor: Takeshi Ito, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/186,944

(22) Filed: Aug. 6, 2008

(65) Prior Publication Data

US 2009/0040598 A1 Feb. 12, 2009

(30) Foreign Application Priority Data

Aug. 10, 2007 (JP) ............................. 2007-210034

(51) Int. Cl.
*G02F 1/35* (2006.01)
*G02F 2/02* (2006.01)
*G02B 6/04* (2006.01)

(52) U.S. Cl. .................. 359/332; 359/326; 385/115

(58) Field of Classification Search ......... 359/326–332; 385/115–121
See application file for complete search history.

(56) References Cited

U.S. PATENT DOCUMENTS 5,803,575 A * 9/1998 Ansems et al. ............... 362/554
2006/0279950 A1 * 12/2006 Hama et al. .................. 362/257
2007/0092184 A1 * 4/2007 Hama et al. ................... 385/76
2008/0262316 A1 * 10/2008 Ajima et al. ................ 600/178

FOREIGN PATENT DOCUMENTS

EP 1780564 A2 * 5/2007
JP 2006-314686 11/2006

* cited by examiner

*Primary Examiner*—Daniel Petkovsek
(74) *Attorney, Agent, or Firm*—Scully, Scott, Murphy & Presser, P.C.

(57) ABSTRACT

An optical fiber lighting apparatus includes an exciting light source, a first optical fiber, a second optical fiber, a wavelength conversion unit, and a reflecting member. The first optical fiber guides the exciting light emitted from the exciting light source. The wavelength conversion unit receives the exciting light exiting from the first optical fiber to generate a wavelength-converted light having a wavelength different from that of the exciting light. The second optical fiber guides at least part of the wavelength-converted light generated by the wavelength conversion unit. The reflecting member reflects, of the reflected scattered light and/or the wavelength-converted light generated by the wavelength conversion unit, at least part of light that has not directly struck the incident region of the second optical fiber, toward the incident region of the second optical fiber.

18 Claims, 7 Drawing Sheets

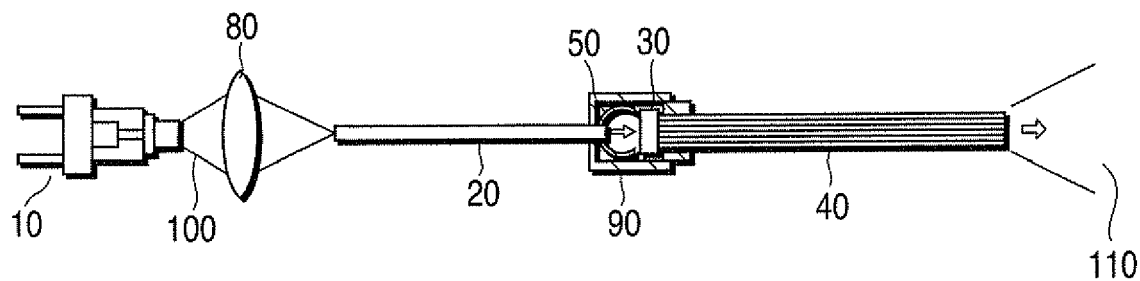
F I G. 1
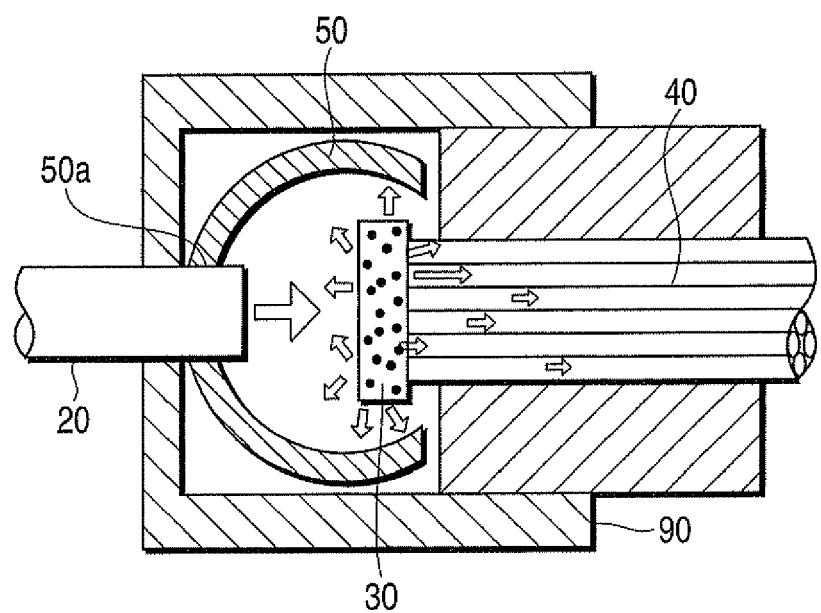
F I G. 2

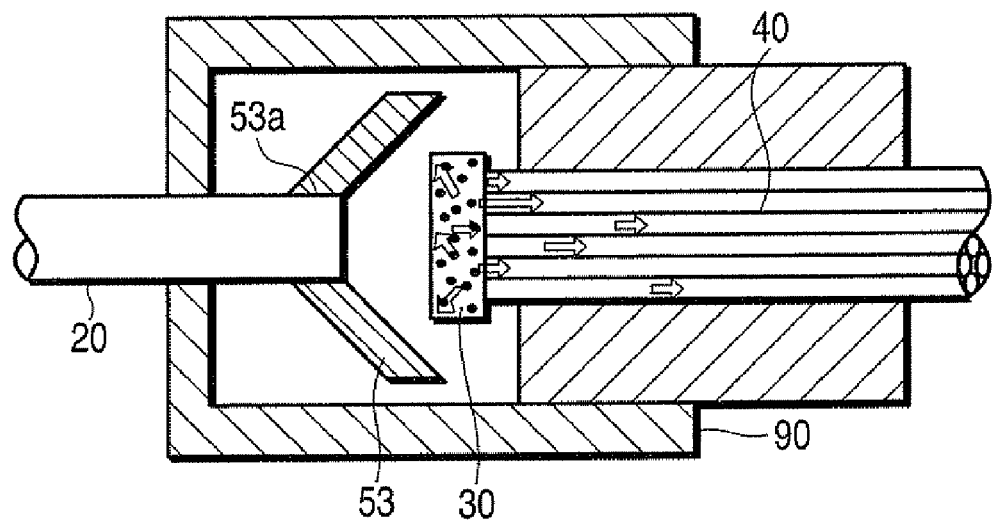
F I G. 7
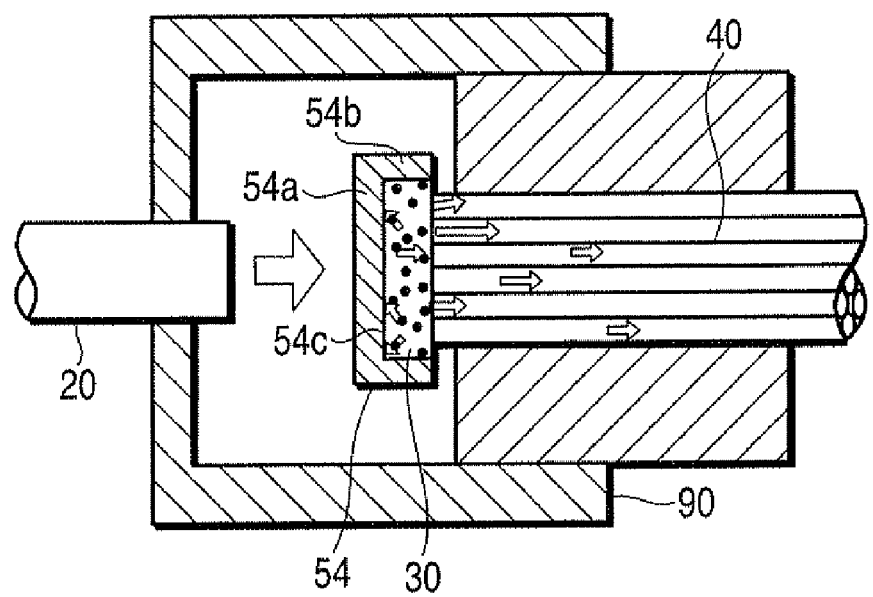
F I G. 8

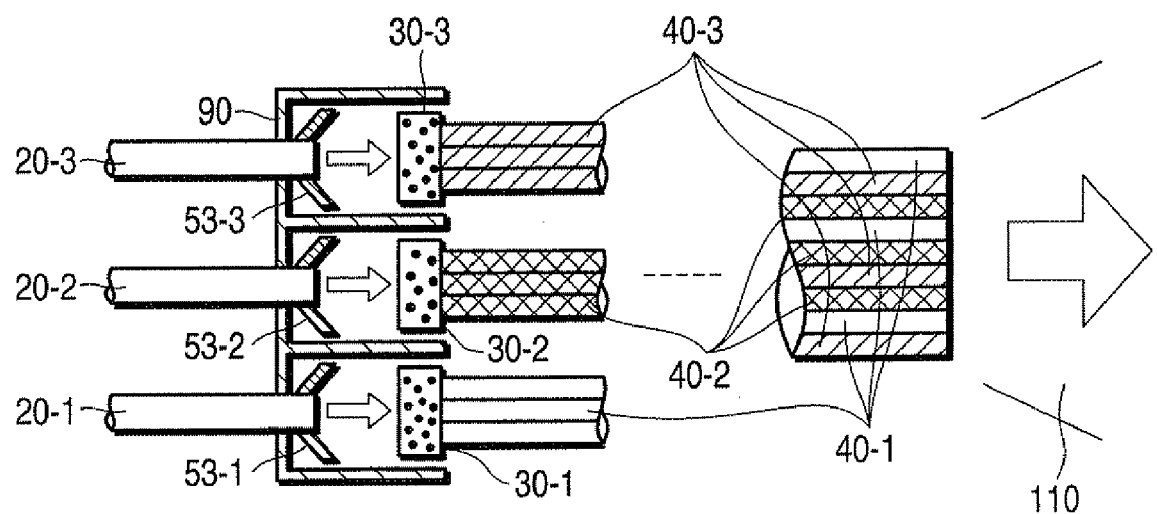
F I G. 11
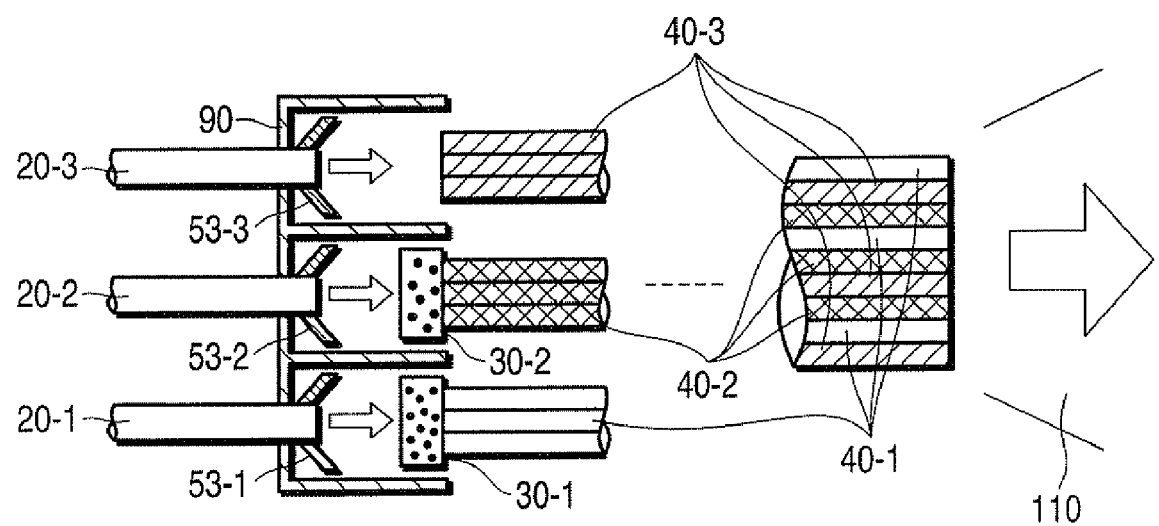
F I G. 12

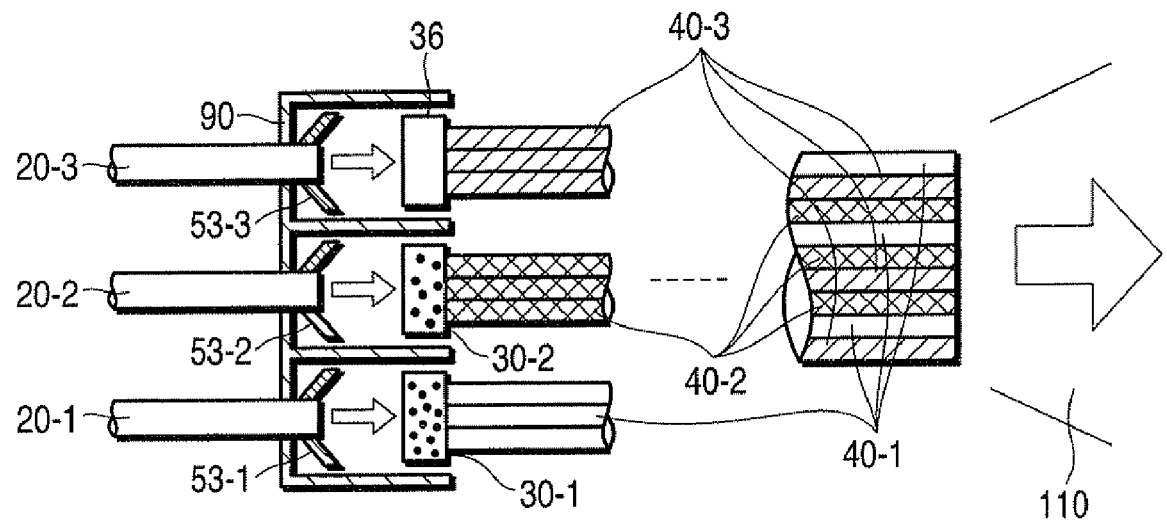
F I G. 13
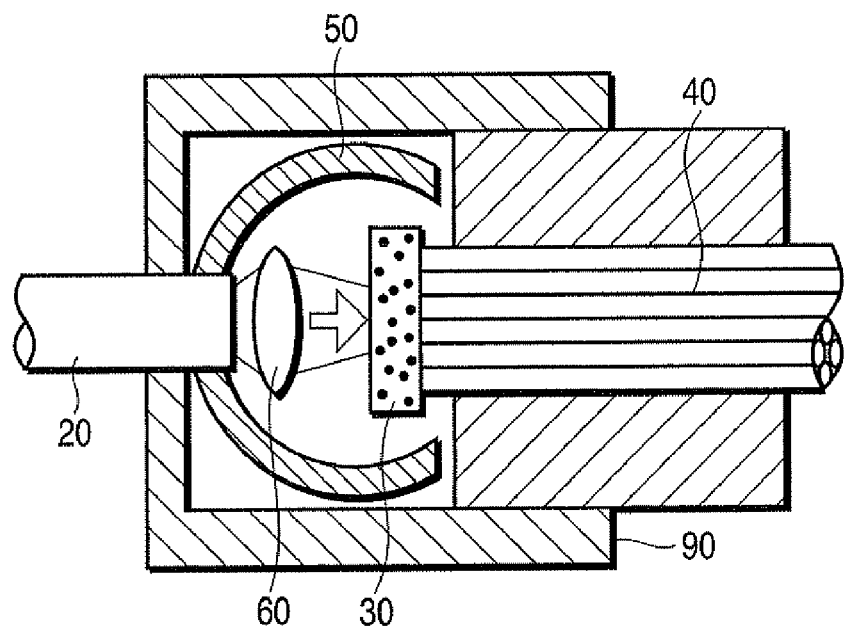
F I G. 14

OPTICAL FIBER LIGHTING APPARATUS

CROSS-REFERENCE TO RELATED APPLICATIONS

This application is based upon and claims the benefit of priority from prior Japanese Patent Application No. 2007-210034, filed Aug. 10, 2007, the entire contents of which are incorporated herein by reference.

BACKGROUND OF THE INVENTION

1. Field of the Invention

The present invention relates to an optical fiber lighting apparatus.

2. Description of the Related Art

There has been proposed an optical fiber lighting apparatus that has LEDs arranged at the proximal end portion of an endoscope and guides light to the light-emitting unit at the distal end of the endoscope via an insertion portion by using a fiber bundle. The fiber bundle is a single bundle on the endoscope distal end side but is separated into three parts on the light source side, which are respectively and directly connected to the LEDs that emit red light, green light, and blue light.

This optical fiber lighting apparatus guides illumination light from the endoscope proximal end portion to the endoscope distal end portion by the fiber bundle, and uses only lenses at a light incident portion that causes light emitted from the LEDs to strike the separated incident ends of the fiber bundle. Accordingly, light that is emitted from the LEDs and does not strike the lenses are not used. The light guide efficiency of the system is poor, and sufficiently bright illumination light is hard to obtain.

BRIEF SUMMARY OF THE INVENTION

An object of the present invention is to provide an optical fiber lighting apparatus that provides sufficiently bright illumination light.

An optical fiber lighting apparatus according to the present invention comprises: an exciting light source that emits exciting light; a first optical fiber that guides the exciting light emitted from the exciting light source; a wavelength conversion unit that receives the exciting light exiting from the first optical fiber to generate a wavelength converted light having a wavelength different from that of the exciting light; a second optical fiber that guides at least part of the wavelength converted light generated by the wavelength conversion unit; and a reflecting member that reflects, of reflected scattered light and/or the wavelength converted light generated by the wavelength conversion unit, at least part of light that has not directly struck the incident region of the second optical fiber, toward an incident region of the second optical fiber.

Advantages of the invention will be set forth in the description that follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing an optical fiber lighting apparatus according to the first embodiment of the present invention;

FIG. 2 is an enlarged view of a phosphor unit shown in FIG. 1 and the peripheral part of a reflecting member;

FIG. 7 is a view showing an optical fiber lighting apparatus according to the third modification of the first embodiment of the present invention;

FIG. 8 is a view showing an optical fiber lighting apparatus according to the fourth modification of the first embodiment of the present invention;

FIG. 11 is an enlarged view of the peripheral part of the phosphor unit shown in FIG. 10;

FIG. 12 is a view showing an optical fiber lighting apparatus according to the fourth embodiment of the present invention;

FIG. 13 is a view showing an optical fiber lighting apparatus according to a modification of the fourth embodiment of the present invention; and FIG. 14 is a view showing a modification that can be applied to each embodiment of the present invention.

DETAILED DESCRIPTION OF THE INVENTION

Figure 3:
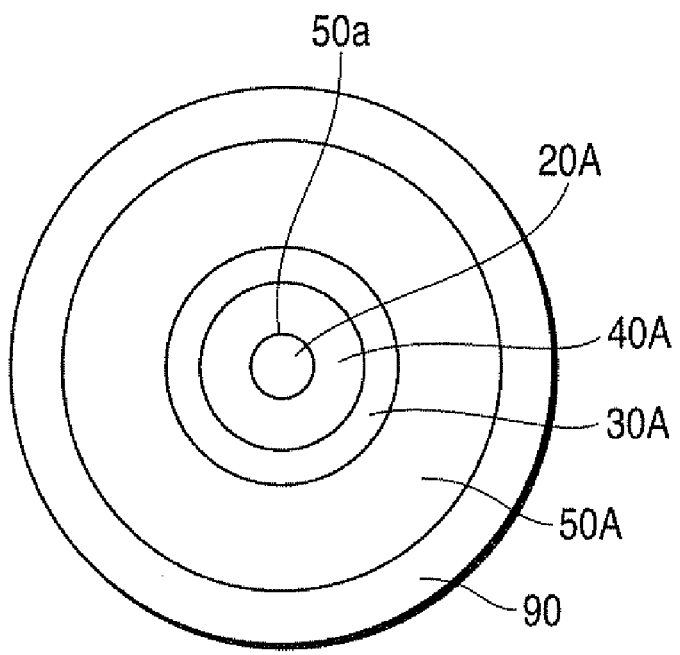
FIG. 3 is a view obtained by projecting the exit region of a single fiber, the effective wavelength conversion region of the phosphor unit, the effective incident region of a fiber bundle, and the reflecting region of a reflecting member onto a plane perpendicular to an optical axis at the exit end of the single fiber.

The embodiments of the present invention will be described below with reference to the views of the accompanying drawing.

First Embodiment

FIG. 1 shows an optical fiber lighting apparatus according to the first embodiment of the present invention. As shown in FIG. 1, the optical fiber lighting apparatus includes a semiconductor laser 10 as an exciting light source that emits exciting light 100, a single fiber 20 as the first optical fiber that guides the exciting light 100 emitted from the semiconductor laser 10, a phosphor unit 30 as a wavelength conversion unit that receives the exciting light 100 exiting from the single fiber 20 to generate fluorescence as wavelength-converted light having a wavelength different from the exciting light 100, and a fiber bundle 40 as the second optical fiber that guides at least part of the wavelength-converted light, i.e., the fluorescence, generated from the phosphor unit 30. The semiconductor laser 10 may be, for example, a violet semiconductor laser. The laser to be used is not limited to this, and another type of semiconductor laser can be used. The phosphor unit 30 includes different types of phosphors, which are mixed with a resin. The phosphor unit 30 emits different types of fluorescences in accordance with the reception of exciting light. These types of fluorescences combine to become white light. The fiber bundle 40 guides the incident fluorescence, and causes white illumination light 110 to exit from the exit end. The optical fiber lighting apparatus further includes a reflecting member 50 that reflects, of the reflected scattered light generated by the phosphor unit 30 and/or the fluorescence generated by the phosphor unit 30, at least part of light that has not directly struck the incident region of the fiber bundle 40, toward the incident region of the fiber bundle 40. In this case, the reflected scattered light means either or both of the light reflected by the phosphor unit 30 and the light scattered by the phosphor unit 30. A condenser lens 80 is placed between the semiconductor laser 10 and the single fiber 20. The condenser lens 80 focuses the exciting light 100 emitted from the semiconductor laser 10 onto the incident region of the single fiber 20.

FIG. 2 is an enlarged view of the phosphor unit 30 and the peripheral part of the reflecting member 50. As shown in FIG. 2 in detail, the phosphor unit 30 is fixed on the incident end of the fiber bundle 40. The reflecting member 50 has an opening 50a through which exciting light exiting from the single fiber 20 passes. The single fiber 20 extends through the opening 50a of the reflecting member 50. The reflecting member 50 is shaped so that the inner surface side of a shape obtained by cutting part of a spherical surface at a plane serves as a reflecting surface. The incident end of the fiber bundle 40 is placed on an axis that passes through the center of the spherical surface and is perpendicular to the plane. A light-shielding member 90 is placed around the phosphor unit 30 and the reflecting member 50 to prevent, of the reflected scattered light and/or the wavelength-converted light generated by the phosphor unit 30, dissipation of light that has not struck the fiber bundle 40.

FIG. 3 is a view obtained by projecting an exit region 20A of the single fiber 20, an effective wavelength conversion region 30A of the phosphor unit 30, an effective incident region 40A of the fiber bundle 40, and a reflecting region 50A of the reflecting member 50 onto a plane perpendicular to an optical axis at the exit end of the single fiber 20. As shown in FIG. 3, the exit region 20A of the single fiber 20, the effective wavelength conversion region 30A of the phosphor unit 30, the effective incident region 40A of the fiber bundle 40, and the reflecting region 50A of the reflecting member 50 all have circular shapes. The shape of the reflecting region 50A projected onto a plane perpendicular to an optical axis at the exit end of the single fiber 20 is point-symmetrical with respect to the center of the opening 50a. More specifically, this shape is circular. In addition, the effective wavelength conversion region 30A of the phosphor unit 30 projected onto a plane perpendicular to an optical axis at the exit end of the single fiber 20 is point-symmetrical with respect to the center of the exit region 20A of the single fiber 20. More specifically, this shape is circular. The effective incident region 40A of the fiber bundle 40 is larger than the exit region 20A of the single fiber 20. The effective wavelength conversion region 30A of the phosphor unit 30 is larger than the effective incident region 40A of the fiber bundle 40. The region obtained by projecting the reflecting region 50A of the reflecting member 50 onto a plane perpendicular to an optical axis at the incident end of the fiber bundle 40 is larger than the effective wavelength conversion region 30A of the phosphor unit 30.

Figure 4:
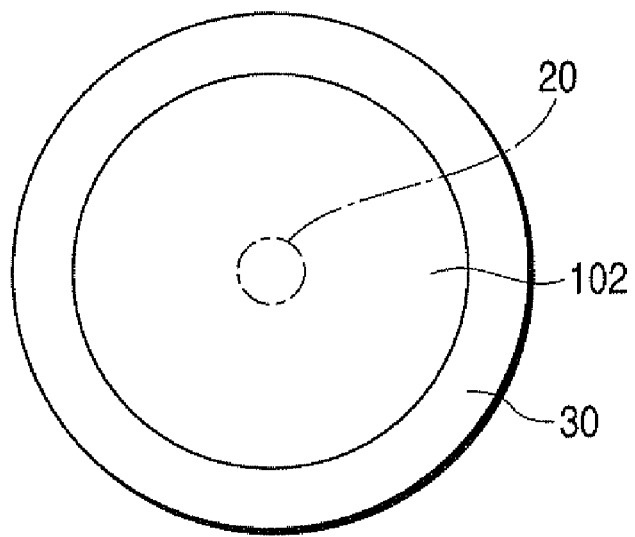
FIG. 4 is a view showing the phosphor unit, the beam spot of exciting light, and the exit end position of the single fiber.

FIG. 4 shows the phosphor unit 30, a beam spot 102 of exciting light, and the exit end position of the single fiber 20. As shown in FIG. 4, the beam spot 102 drawn on the surface of the phosphor unit 30 by exciting light exiting from the single fiber 20 has an almost circular shape centered on the exit end of the single fiber 20.

Referring to FIG. 1, the exciting light 100 emitted from the semiconductor laser 10 is focused by the condenser lens 80 and strikes the incident region of the single fiber 20. The exciting light 100 striking the single fiber 20 is guided by the single fiber 20 and exits from the exit end of the single fiber 20. The exciting light 100 exiting from the single fiber 20 strikes the phosphor unit 30. Part of the exciting light 100 enters the phosphor unit 30 and is converted into fluorescence having a longer wavelength than the exciting light 100 by the phosphor in the phosphor unit 30. Part of the fluorescence strikes the fiber bundle 40 and exits as the white illumination light 110 from the exit end of the fiber bundle 40.

Referring to FIG. 2, part of the exciting light 100 striking the phosphor unit 30 is converted into fluorescence, as described above. Another part of the exciting light 100 passes through the phosphor unit 30 and strikes the fiber bundle 40. The light then exits from the exit end of the fiber bundle 40. Another part of the exciting light 100 is reflected or scattered by the phosphor unit 30 in accordance with the incident direction to become reflected scattered light. This light exits in a direction other than that of the incident end of the fiber bundle 40. Part of the fluorescence emitted from the phosphor unit 30 strikes the fiber bundle 40, as described above. The remaining part of the fluorescence exits in a direction other than that of the incident end of the fiber bundle 40. The fluorescence emitted from the phosphor unit 30 exits in all directions regardless of the incident direction of the exciting light 100. For this reason, much of the fluorescence exits in a direction other than that of the incident end of the fiber bundle 40. The light-shielding member 90 provided outside the phosphor unit 30 prevents the fluorescence and exciting light exiting in a direction other than that of the incident end of the fiber bundle 40 from dissipating to the outside. Part of the reflected scattered light is reflected by the reflecting member 50. Part of the reflected light then strikes the phosphor unit 30 again. Part of the light enters the phosphor unit 30 and is converted into fluorescence having a longer wavelength than the exciting light 100 by the phosphor in the phosphor unit 30. Part of the fluorescence strikes the fiber bundle 40. Part of the fluorescence exiting in a direction other than that of the incident end of the fiber bundle 40 is reflected by the reflecting member 50. Part of the reflected fluorescence strikes the phosphor unit 30. Part of the fluorescence enters the phosphor unit 30 and partly strikes the fiber bundle 40. As a consequence, a large amount of fluorescence strikes the fiber bundle 40. This can improve the light guide efficiency of the overall optical fiber lighting apparatus and obtain bright illumination light.

[First Modification]

Figure 5:
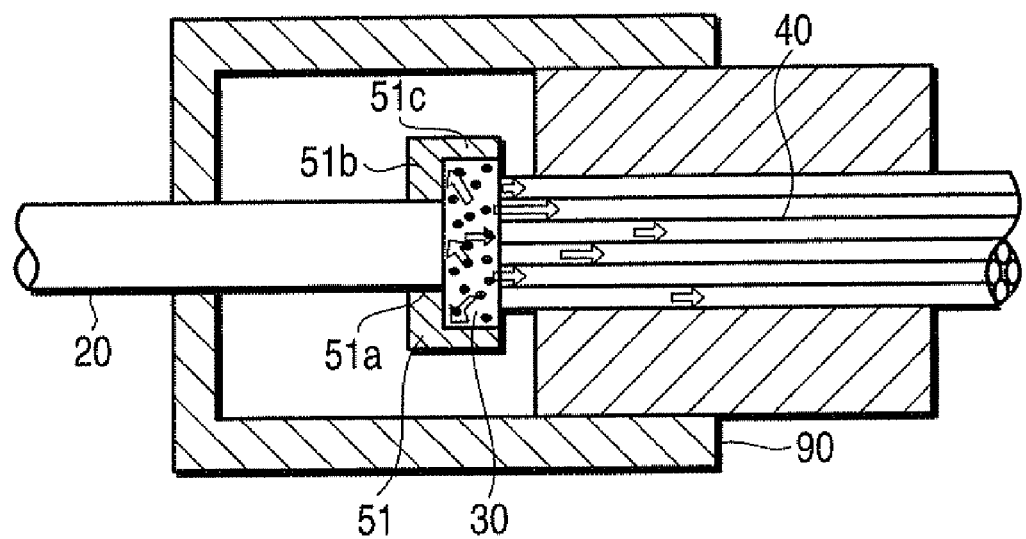
FIG. 5 is a view showing an optical fiber lighting apparatus according to the first modification of the first embodiment of the present invention.

FIG. 5 shows an optical fiber lighting apparatus according to the first modification of the first embodiment of the present invention. As shown in FIG. 5, the optical fiber lighting apparatus includes a reflecting member 51 directly fixed to the phosphor unit 30 in place of the reflecting member 50. The reflecting member 51 comprises a bottom portion 51b having a circular plane and a circular tubular side surface portion 51c. The bottom portion 51b has an opening 51a in its center. The single fiber 20 is inserted in the opening 51a. The exit end of the single fiber 20 is in contact with the phosphor unit 30.

In this modification, since the exit end of the single fiber 20 is in contact with the phosphor unit 30, reflected scattered light is hardly generated. In addition, since the reflecting member 51 is directly fixed to the phosphor unit 30, fluorescence exiting in a direction other than that of the incident end of the fiber bundle 40 is efficiently returned to the phosphor unit 30. As a consequence, a large amount of fluorescence strikes the fiber bundle 40.

[Second Modification]

Figure 6:
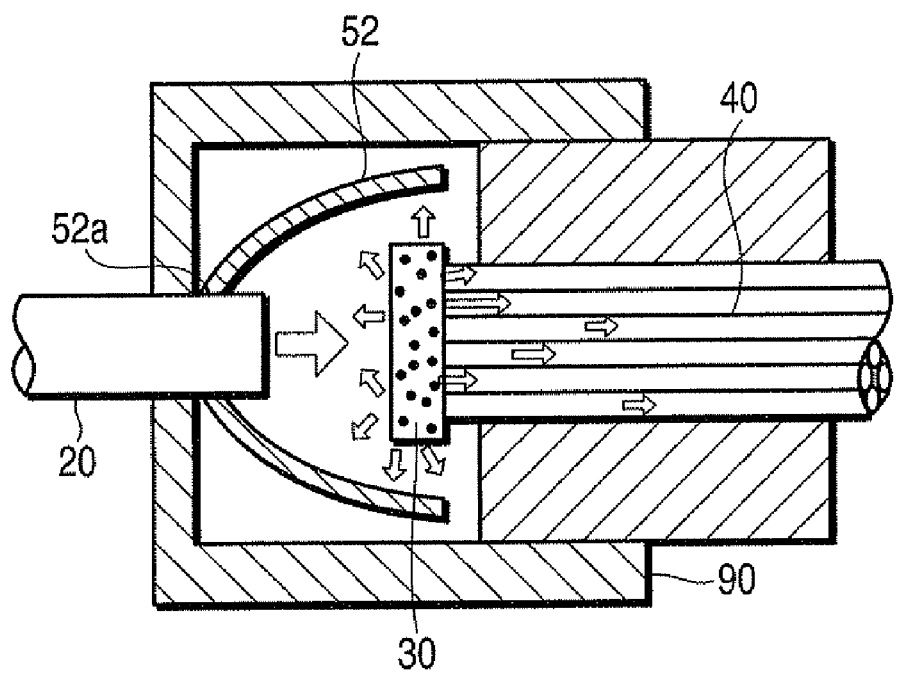
FIG. 6 is a view showing an optical fiber lighting apparatus according to the second modification of the first embodiment of the present invention.

FIG. 6 shows an optical fiber lighting apparatus according to the second modification of the first embodiment of the present invention. As shown in FIG. 6, the optical fiber lighting apparatus includes a reflecting member 52 having a reflecting surface with a shape of a parabolic surface in place of the reflecting member 50. The reflecting member has an opening 52a in the vertex of the parabolic surface. The single fiber 20 is inserted in the opening 52a. The incident end of the fiber bundle 40 is placed on the central axis of the parabolic surface. The central axis of the parabolic surface means a rotation axis about which a parabola is rotated to form the parabolic surface.

In this modification, of the reflected scattered light generated by the phosphor unit 30, the reflected scattered light generated near the optical axis of exciting light in the wavelength conversion unit is reflected by the reflecting member 52 to become almost parallel light and strike the incident end of the fiber bundle 40. This improves the coupling efficiency between the fiber bundle 40 and incident light, and hence can efficiently guide the light to the incident end of the fiber bundle 40.

[Third Modification]

FIG. 7 shows an optical fiber lighting apparatus according to the third modification of the first embodiment of the present invention. As shown in FIG. 7, the optical fiber lighting apparatus includes a reflecting member 53 having a reflecting surface with a conical shape in place of the reflecting member 50. The reflecting member has an opening 53a in the vertex of the conical surface. The single fiber 20 is inserted in the opening 53a.

[Fourth Modification]

FIG. 8 shows an optical fiber lighting apparatus according to the fourth modification of the first embodiment of the present invention. As shown in FIG. 8, the optical fiber lighting apparatus includes a reflecting member 54 directly fixed to the phosphor unit 30 in place of the reflecting member 50. The reflecting member 54 is obtained by forming a dielectric multilayer film 54c on the surface of a member that has a bottom portion 54a with a circular plane and a circular tubular side surface portion 54b and is transparent to exciting light. The dielectric multilayer film 54c transmits light near the wavelength of the exciting light but reflects fluorescence. For this reason, the reflecting member 54 has an opening through which exciting light exiting from the single fiber 20 passes.

The exciting light exiting from the single fiber 20 is transmitted through the bottom portion 54a and dielectric multilayer film 54c of the reflecting member 54 and strikes the phosphor unit 30. Part of the fluorescence emitted from the phosphor unit 30 strikes the fiber bundle 40. The remaining part of the fluorescence exits in a direction other than that of the incident end of the fiber bundle 40. Most of the fluorescence exiting in a direction other than that of the incident end of the fiber bundle 40 is reflected by the dielectric multilayer film 54c of the reflecting member 54 and returns into the phosphor unit 30. Part of the reflected light strikes the fiber bundle 40.

In this modification, since the reflecting member 54 is directly fixed to the phosphor unit 30, fluorescence exiting in a direction other than that of the incident end of the fiber bundle 40 is efficiently returned to the phosphor unit 30. Much of the fluorescence then strikes the fiber bundle 40.

Note that these modifications can be combined with each other. When, for example, a reflecting member is to be directly fixed to a phosphor unit as in the fourth modification, the shape of the reflecting member can be that of part of a spherical surface as in the first embodiment, or can be a parabolic shape as in the second modification. In this case, the shape of the phosphor unit conforms to the reflecting surface.

Second Embodiment

Figure 9:
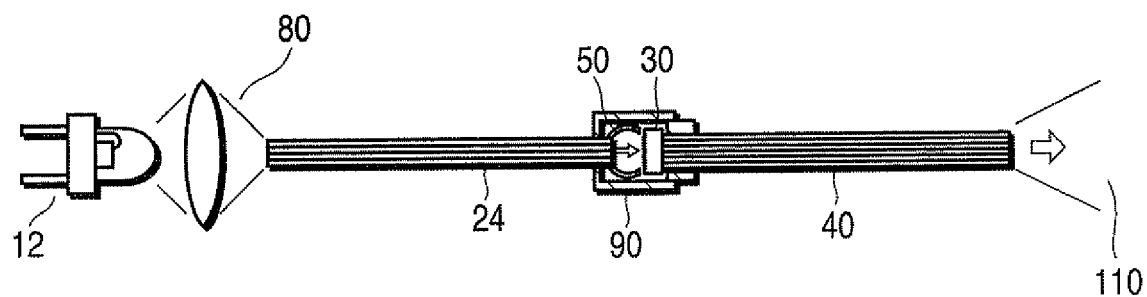
FIG. 9 is a view showing an optical fiber lighting apparatus according to the second embodiment of the present invention.

FIG. 9 shows an optical fiber lighting apparatus according to the second embodiment of the present invention. The optical fiber lighting apparatus of this embodiment has the same basic structure as that in the first embodiment. As shown in FIG. 9, however, this apparatus includes an LED 12 in place of the semiconductor laser 10 as an exciting light source and a fiber bundle 24 in place of the single fiber 20 as the first optical fiber. Using the LED 12 as an exciting light source can simultaneously achieve low cost and eye safety. In addition, this can simplify the system by eliminating the necessity of a feedback circuit for optical outputs. Furthermore, using the fiber bundle 24 as the first optical fiber that guides exciting light can efficiently guide LED light and apply it to a phosphor unit 30.

In this arrangement, at the exit end of the fiber bundle 24, exciting light exits from each single fiber constituting the fiber bundle 24. In this case, an optical axis at the exit end of the fiber bundle 24 is defined by the exit direction of light in which light exiting from the fiber bundle 24 exhibits its peak intensity and the barycentric position of a light intensity distribution at the exit end of the fiber bundle 24.

In this embodiment, the exciting light source comprises the lamp-type LED 12 having a dome lens. However, the embodiment is not limited to this. The exciting light source may comprise a current confinement type LED light source or SLD (Super Luminescent Diode) light source. Using a current confinement type LED light source or SLD light source can improve the coupling efficiency with an optical fiber as compared with general LED light. This can therefore improve the utilization efficiency of exciting light.

Third Embodiment

Figure 10:
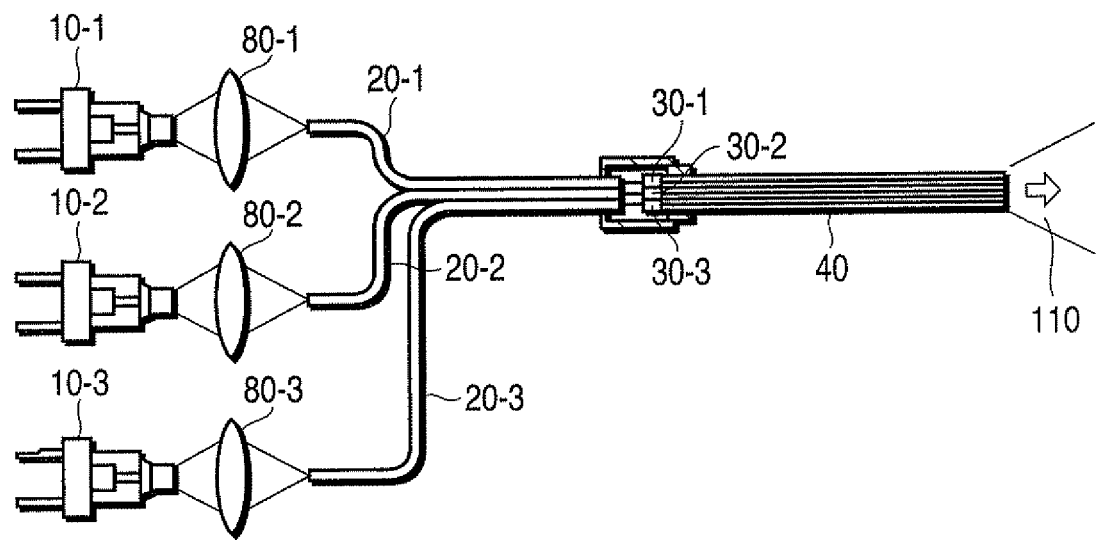
FIG. 10 is a view showing an optical fiber lighting apparatus according to the third embodiment of the present invention.

FIG. 10 shows an optical fiber lighting apparatus according to the third embodiment of the present invention. The optical fiber lighting apparatus according to this embodiment has the same basic structure as that of the first embodiment. As shown in FIG. 10, however, this apparatus includes, in place of the semiconductor laser 10, semiconductor lasers 10-1, 10-2, and 10-3 that respectively emit exciting light beams. The apparatus also includes, in place of the single fiber 20, single fibers 20-1, 20-2, and 20-3 that respectively guide exciting light beams emitted from the semiconductor lasers 10-1, 10-2, and 10-3. The apparatus further includes, in place of the phosphor unit 30, phosphor units 30-1, 30-2, and 30-3 that respectively receive the exciting light beams exiting from the single fibers 20-1, 20-2, and 20-3 to generate wavelength-converted light beams having different wavelengths. The number of phosphor units 30-1, 30-2, and 30-3 is the same as that of single fibers 20-1, 20-2, and 20-3. In addition, condenser lenses 80-1, 80-2, and 80-3 that respectively focus the exciting light beams emitted from the semiconductor lasers 10-1, 10-2, and 10-3 onto the incident regions of the single fibers 20-1, 20-2, and 20-3 are arranged between the semiconductor lasers 10-1, 10-2, and 10-3 and the single fibers 20-1, 20-2, and 20-3 in place of the condenser lens 80.

The fluorescences emitted from the phosphor units 30-1, 30-2, and 30-3 have different wavelengths. These types of fluorescences combine to become white light. The wavelengths of exciting light beams are selected in accordance with the exciting characteristics of phosphors in the phosphor units 30-1, 30-2, and 30-3. For example, it is possible to perform efficient wavelength conversion by using near ultra violet light or violet light with a wavelength of about 370 nm to 420 nm for phosphors such as $BaMgAl_{10}O_{17}$: Eu (blue), $BaMgAl_{10}O_{17}$: Eu, Mn (green), and $La_2O_2S$: Eu (red). Alternatively, it is possible to perform efficient wavelength conversion by using blue light with a wavelength of about 470 nm for phosphors such as YAG: Ce (yellow) and Ba orthosilicate: Eu (yellow).

FIG. 11 is an enlarged view of the peripheral parts of the phosphor units 30-1, 30-2, and 30-3. As shown in FIG. 11, the phosphor units 30-1, 30-2, and 30-3 are isolated from each other by a light-shielding member 90 that has a light-shielding property for exciting light and/or wavelength-converted light. Exciting light beams exiting from the single fibers 20-1, 20-2, and 20-3 respectively strike the corresponding phosphor units, but do not strike the non-corresponding phosphor units. A fiber bundle 40 comprises partial fiber bundles 40-1, 40-2, and 40-3 respectively connected to the phosphor units 30-1, 30-2, and 30-3. The single fibers 20-1, 20-2, and 20-3 are respectively provided with reflecting members 53-1, 53-2, and 53-3 that reflect at least parts of light beams, of the reflected scattered light generated by the phosphor units 30-1, 30-2, and 30-3 and/or the fluorescences emitted from the phosphor units 30-1, 30-2, and 30-3, which have not directly struck the incident regions of the partial fiber bundles 40-1, 40-2, and 40-3 toward the incident regions of the partial fiber bundles 40-1, 40-2, and 40-3. The reflecting members 53-1, 53-2, and 53-3 each are the same as the reflecting member 53 described in the third modification of the first embodiment.

The fiber bundle 40 is configured so that the positional relationship between the incident ends of the unit fibers constituting the fiber bundle differs from the positional relationship between the exit ends. The fiber bundle 40 is also configured so that the barycenters of the output intensities of fluorescences having different wavelengths that are emitted from the phosphor units 30-1, 30-2, and 30-3 and strike the fiber bundle 40 almost coincide with the center of the effective exit region of the fiber bundle 40 at the exit end of the fiber bundle 40. The numbers of unit fibers contained in the partial fiber bundles 40-1, 40-2, and 40-3 may be equal to each other. The ratio among the numbers of unit fibers contained in the partial fiber bundles 40-1, 40-2, and 40-3 may be adjusted in accordance with the emission intensities of the respective fluorescences so that the fluorescences having different wavelengths exiting from the fiber bundle 40 combine to become light of a desired color, e.g., white. That is, it is possible to adjust illumination light to a desired color by adjusting the emission intensities of the semiconductor lasers 10-1, 10-2, and 10-3 while equalizing the numbers of unit fibers contained in the partial fiber bundles 40-1, 40-2, and 40-3. Alternatively, it is possible to adjust illumination light to a desired color by adjusting the numbers of unit fibers contained in the partial fiber bundles 40-1, 40-2, and 40-3 while equalizing the driving conditions for the exciting light sources.

The exciting light beams emitted from the semiconductor lasers 10-1, 10-2, and 10-3 respectively strike the corresponding phosphor units 30-1, 30-2, and 30-3 via the single fibers 20-1, 20-2, and 20-3. The phosphor units 30-1, 30-2, and 30-3 respectively emit fluorescences having different wavelengths upon receiving exciting light beams exiting from the single fibers 20-1, 20-2, and 20-3. The fluorescences emitted from the phosphor units 30-1, 30-2, and 30-3 exit via the fiber bundle 40.

In this arrangement, light beams having different wavelengths can be emitted independently.

Although the three phosphor units are coupled to each other in this embodiment, monochromatic phosphor units can be used. This arrangement allows to adjust the number of phosphors to be excited in accordance with an application. If, for example, a dark condition is required, only a small number of phosphor units are excited. If a bright condition is required, many phosphor units are excited. This allows the output level to be adjusted without changing the color.

Fourth Embodiment

FIG. 12 shows an optical fiber lighting apparatus according to the fourth embodiment of the present invention. The optical fiber lighting apparatus of this embodiment has the same basic structure as that of the third embodiment except that the phosphor unit 30-3 is omitted from the phosphor units 30-1, 30-2, and 30-3 in the arrangement of the third embodiment, as shown in FIG. 12. That is, the optical fiber lighting apparatus of this embodiment includes only phosphor units 30-1 and 30-2. The number of phosphor units 30-1 and 30-2 is smaller than that of unit fibers 20-1, 20-2, and 20-3. With this arrangement, parts of exciting light beams emitted from semiconductor lasers 10-1 and 10-2 respectively strike the unit fibers 20-1 and 20-2, and parts of exciting light beams exiting from the unit fibers 20-1 and 20-2 are wavelength-converted by the phosphor units 30-1 and 30-2 and strike the incident region of the fiber bundle 40. The light then exits from the fiber bundle 40. Part of the exciting light emitted from the semiconductor laser 10-3 strikes the unit fiber 20-3. Part of the exciting light exiting from the unit fiber 20-3 directly strikes the incident region of the fiber bundle 40 without being wavelength-converted, and exits from the exit end of the fiber bundle 40. The fiber bundle 40 guides part of the exciting light exiting from the unit fiber 20-3 in addition to part of fluorescence as wavelength-converted light. That is, the optical fiber lighting apparatus is configured to make exciting light exit from the fiber bundle 40.

As shown in FIG. 13, a light diffusion unit 36 having a light diffusion material can be provided at a portion where light that is emitted from the semiconductor laser 10-3 and exits via the unit fiber 20-3 strikes the partial fiber bundle 40-3. That is, the light diffusion unit 36 can be further provided at the incident region of the partial fiber bundle 40-3 of the fiber bundle 40 between the unit fiber 20-3, from which part of exciting light directly striking the incident region exits, and the partial fiber bundle 40-3. This can shorten the coherent length of exciting light exiting from the exit end of the fiber bundle 40 as compared with exciting light emitted from the semiconductor laser 10-3. If laser light is used as exciting light, an observation target having a periodic pattern may generate an interference image or the like, resulting in difficulty in observation. Inserting an optical member, a diffusion plate, or the like that disturbs the phase relationship between exciting light beams will shorten the coherent length of the exciting light. This can suppress the generation of an interference image corresponding to the period of the observation target. Exciting light directly entering the eyes of an observer may affect the sense of sight. However, shortening the coherence length can avoid such danger and implement eye-safe design.

Although the embodiments of the present invention have been described with reference to the views of the accompanying drawing, the present invention is not limited to these embodiments. The embodiments can be variously modified and changed within the spirit and scope of the invention.

For example, in all the embodiments described above, as shown in FIG. 14, an optical member 60 such as a lens that focuses exciting light exiting from the single fiber 20 can be provided between the single fiber 20 and the phosphor unit 30. This arrangement can guide light more efficiently by focusing exciting light exiting from the single fiber 20 using the optical member 60 and applying the light onto the phosphor unit 30.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical fiber lighting apparatus comprising:
   an exciting light source that emits exciting light;
   a first optical fiber that guides the exciting light emitted from the exciting light source;
   a wavelength conversion unit that receives the exciting light exiting from the first optical fiber to generate a wavelength-converted light having a wavelength different from that of the exciting light;
   a second optical fiber that guides at least part of the wavelength-converted light generated by the wavelength conversion unit; and
   a reflecting member that reflects, of reflected scattered light and/or the wavelength-converted light generated by the wavelength conversion unit, at least part of any such light that has not directly struck the incident region of the second optical fiber, toward an incident region of the second optical fiber.

2. An optical fiber lighting apparatus comprising:
   an exciting light source that emits exciting light;
   a first optical fiber that guides the exciting light emitted from the exciting light source;
   a wavelength conversion unit that receives the exciting light exiting from the first optical fiber to generate a wavelength-converted light having a wavelength different from that of the exciting light;
   a second optical fiber that guides at least part of the wavelength-converted light generated by the wavelength conversion unit; and
   a reflecting member that reflects, of reflected scattered light and/or the wavelength-converted light generated by the wavelength conversion unit, at least part of any such light that has not directly struck the incident region of the second optical fiber, toward an incident region of the second optical fiber;
   wherein the second optical fiber comprises a fiber bundle, an effective incident region of the fiber bundle is larger than an exit region of the first optical fiber, an effective wavelength conversion region of the wavelength conversion unit is larger than the effective incident region of the fiber bundle, and a region obtained by projecting an effective reflecting region of the reflecting member onto a plane perpendicular to an optical axis at an incident end of the second optical fiber is larger than the effective wavelength conversion region of the wavelength conversion unit.

3. The apparatus according to claim 2, wherein the reflecting member includes an opening through which the exciting light exiting from the first optical fiber passes.

4. The apparatus according to claim 3, wherein a shape of a reflecting region of the reflecting member that is projected onto a plane perpendicular to an optical axis at the exit end of the first optical fiber is point-symmetrical with respect to a center of the opening.

5. The apparatus according to claim 4, wherein a shape of the effective conversion region of the wavelength conversion unit that is projected onto a plane perpendicular to an optical axis at the exit end of the first optical fiber is point-symmetrical with respect to a center of the exit region of the first optical fiber.

6. The apparatus according to claim 3, further comprising a light-shielding member that prevents, of the reflected scattered light and/or the wavelength-converted light generated by the wavelength conversion unit, dissipation of light that has not struck the second optical fiber.

7. The apparatus according to claim 3, wherein the reflecting member is directly fixed to the wavelength conversion unit.

8. The apparatus according to claim 3, wherein the reflecting member has a reflecting surface with the same shape as that of a shape obtained by cutting part of a spherical surface at a plane on an inner surface side, and the incident end of the second optical fiber is placed on an axis that passes through a center of the spherical surface and is perpendicular to the plane.

9. The apparatus according to claim 3, wherein the reflecting member includes a reflecting surface having shape of a parabolic surface, and the incident end of the second optical fiber is placed on a central axis of the parabolic surface.

10. The apparatus according to claim 2, wherein the exciting light source comprises a laser light source, and the first optical fiber comprises a single fiber.

11. The apparatus according to claim 2, wherein the exciting light source comprises an LED light source, and the first optical fiber comprises a fiber bundle.

12. The apparatus according to claim 2, comprising exciting light sources that respectively emit exciting light beams, first optical fibers that respectively guide the exciting light beams emitted from the exciting light sources, wavelength conversion units that respectively receive the exciting light beams exiting from the first optical fibers to generate wavelength-converted light beams having different wavelengths, and reflecting members that reflect, of reflected scattered light beams and/or the wavelength-converted light beams generated by the wavelength conversion units, at least parts of light beams that have not directly struck the incident region of the second optical fiber, toward the incident region of the second optical fiber, the second optical fiber guiding at least parts of the wavelength-converted light beams generated by the wavelength conversion units.

13. The apparatus according to claim 12, wherein the number of the wavelength conversion units are the same as that of the first optical fibers, and the wavelength conversion units respectively receive the exciting light beams exiting from the first optical fibers to generate wavelength-converted light beams having different wavelengths.

14. The apparatus according to claim 13, wherein the wavelength conversion units are isolated from each other by a light-shielding member having a light shielding property with respect to the exciting light beams and/or the wavelength-converted light beams, and the exciting light beams exiting from the first optical fibers strike corresponding wavelength conversion units but do not strike non-corresponding wavelength conversion units.

15. The apparatus according to claim 12, wherein the second optical fiber comprises a fiber bundle, the fiber bundle is configured so that a positional relationship between incident ends of unit fibers constituting the fiber bundle differs from a positional relationship between exit ends of the unit fibers, and barycenters of output intensities of the wavelength-converted light beams having different wavelengths that have been generated by the wavelength conversion units and have struck the fiber bundle substantially coincide with a center of an effective exit region of the fiber bundle at the exit end of the fiber bundle.

16. The apparatus according to claim 15, wherein the fiber bundle includes partial fiber bundles that are respectively connected to the wavelength conversion units and the ratio among the numbers of unit fibers contained in the partial fiber bundles is adjusted so that the wavelength-converted light beams having different wavelengths combine to become light of a desired color.

17. The apparatus according to claim 12, wherein the number of wavelength conversion units is smaller than the number of first optical fibers, part of the exciting light exiting from at least one of the first optical fibers directly strikes the incident region of the second optical fiber without through the wavelength conversion unit, and the second optical fiber guides the part of the exciting light in addition to the part of the wavelength-converted light.

18. The apparatus according to claim 17, further comprising a light diffusion unit provided between the second optical fiber and the first optical fiber from which exciting light partly to directly strike the incident region of the second optical fiber.

* * * * *